(12) United States Patent
Hobbs et al.

(10) Patent No.: US 7,262,856 B2
(45) Date of Patent: Aug. 28, 2007

(54) MICROSTRUCTURED OPTICAL DEVICE FOR REMOTE CHEMICAL SENSING

(76) Inventors: Douglas S. Hobbs, 1998 Massachusetts Ave., Lexington, MA (US) 02421; Curtis A. Lockshin, 7 Ross Rd., Lexington, MA (US) 02421; James J. Cowan, 9 Winston Rd., Lexington, MA (US) 02421; Robert B. Nilsen, 112 Clift St., Mystic, CT (US) 06355

( * ) Notice: Subject to any disclaimer, the term of this patent is extended or adjusted under 35 U.S.C. 154(b) by 321 days.

(21) Appl. No.: 11/137,701

(22) Filed: May 25, 2005

(65) Prior Publication Data

US 2007/0036680 A1   Feb. 15, 2007

Related U.S. Application Data

(60) Provisional application No. 60/574,494, filed on May 25, 2004.

(51) Int. Cl.
  *G01N 21/00*   (2006.01)
  *C12M 1/34*   (2006.01)
(52) U.S. Cl. .............. 356/436; 356/440; 422/82.05; 422/82.09; 435/287.2; 435/288.7
(58) Field of Classification Search ........ 356/432–440, 356/244, 246; 435/287.2, 288.7; 422/82.05, 422/82.09; 385/10, 37, 129–132
See application file for complete search history.

(56) References Cited

U.S. PATENT DOCUMENTS

| | | | | |
|---|---|---|---|---|
| 3,857,641 A | * | 12/1974 | Gass | 356/438 |
| 4,126,396 A | * | 11/1978 | Hartmann et al. | 356/434 |
| 6,239,875 B1 | * | 5/2001 | Verheijen | 356/436 |
| 6,870,624 B2 | * | 3/2005 | Hobbs et al. | 356/416 |
| 7,118,710 B2 | * | 10/2006 | Cunningham | 422/82.09 |
| 2003/0027328 A1 | * | 2/2003 | Cunningham et al. | 435/287.2 |
| 2003/0210396 A1 | * | 11/2003 | Hobbs et al. | 356/416 |
| 2004/0132172 A1 | * | 7/2004 | Cunningham et al. | 435/287.2 |
| 2006/0285116 A1 | * | 12/2006 | Metcalfe | 356/439 |
| 2007/0097371 A1 | * | 5/2007 | Parker | 356/437 |

* cited by examiner

*Primary Examiner*—Hoa Q. Pham (57) ABSTRACT

A microstructure-based chemical sensor that can be interrogated by a remote observer. The device acts as an electromagnetic wave filter in the optical region of the spectrum, filtering one or more wavelength bands where the band spectral notch location shifts in response to the accumulation of material on the surface of the microstructure sensor. The apparatus has a substrate having a surface relief structure containing dielectric bodies with one or more physical dimensions smaller than the wavelength of the filtered electromagnetic waves, such structures repeated in an array covering at least a portion of the surface of the substrate. A retro-reflecting structure allows interrogation of the sensor over a wide field of view. The device is particularly useful as a water monitoring device in hard to reach locations, and as a chemical warfare or explosives detector that can be read from a safe distance.

34 Claims, 11 Drawing Sheets

MICROSTRUCTURED OPTICAL DEVICE FOR REMOTE CHEMICAL SENSING

CROSS REFERENCE TO RELATED APPLICATION

This application claims priority of Provisional Application Ser. No. 60/574,494, filed on May 25, 2004 entitled "Surface Relief Structure".

FIELD OF THE INVENTION

This invention is in the field of optically-based biological or chemical sensors useful for detecting and identifying chemicals such as pollutants, chemical warfare agents, or biochemical matter such as DNA, proteins, or other bio-molecules.

BACKGROUND OF THE INVENTION

A unique and highly sensitive chemical detection device can be created using guided-mode surface structure hologram optical filters as taught by Hobbs and Cowan in U.S. Pat. Nos. 6,791,757 and 6,870,624, both of which are incorporated herein by reference. Guided mode surface structure filters produce exceptionally narrow optical resonances that can be disturbed by the accumulation of material depositing on the structure surface. This disturbance is detected as a shift in the wavelength of the light resonating within the structural waveguide. The design of both reflection- and transmission-mode wave-guide resonant structures is further taught by Magnusson in U.S. Pat. Nos. 5,216,680, 5,598,300, and 6,154,480, and in the literature by Peng and Morris, "Resonant Scattering from two-dimensional gratings", J. Opt. Soc. Am. A, Vol. 13, No. 5, p. 993, May 1996; Magnusson and Wang, "New Principle for optical filters," Applied Physics Letters, 61, No. 9, p. 1022, August 1992; and Hobbs, "Laser-Line Rejection or Transmission Filters Based on Surface Structures Built on Infrared Transmitting Materials", Proceedings SPIE Vol. 5786, Window and Dome Technologies and Materials IX, March 2005.

The utility of employing a surface structure resonator, or SSR, to detect the presence and concentration of organic chemicals has been demonstrated by Hobbs and Cunningham in U.S. Patent Application Publication Nos. 2002/0168295 and 2004/0132172, and by Cunningham in "Colorimetric resonant reflection as a direct biochemical assay technique", Sensors and Actuators B, Vol. 81, 2002.

The wavelength of light that resonates in an SSR device is dependent on the angle of incidence of the light striking the SSR, and the SSR signal must be observed at a specific viewing angle, an angle equal to the angle of incidence of the interrogating light. To use an SSR to detect chemicals in an environment that is a large distance from the environment of the observer, an SSR sensor must be configured to operate on interrogating light that is incident at an angle very close to zero degrees, or normal to the SSR surface. In addition, the SSR is most commonly configured as a narrow-band reflector where the energy returned to the observer will be small compared to the energy in the broadband interrogating light beam. These considerations limit the practical use of an SSR to detect chemicals at distances of more than a few centimeters, and the use of inexpensive flexible materials such as plastic in the fabrication of SSR sensors.

Historically, applications of label-free sensors have relied primarily on bio-molecules such as antibodies, proteins, or nucleic acids. These biologically derived molecules tend to suffer from instability issues, which arise from sensitivity to changes in temperature, chemical environments, and the like. This invention provides for incorporation of robust, durable, selective capture agents such as molecularly imprinted polymers (MIPS) and other organic/inorganic molecules with selective affinity for target molecules.

Typical chemical and biochemical assays used for environmental monitoring require sample collection in the field, followed by field assays (utilizing portable instruments), or return of samples to a central facility for processing. Such assays cannot be performed in remote locations such as challenging terrain, aquatic environments, space, chemical reaction vessels, or bioreactors. Hence, there are practical limitations to the rate and scope of environmental vigilance, due to cost and logistical issues.

There remains an immediate need for a sensor device with the target selectivity and high sensitivity typical of an SSR that is capable of detecting the concentration of chemicals in an environment that is remote from the observer.

SUMMARY OF THE INVENTION

An optical device that can efficiently reflect an interrogating light beam back to an observer regardless of the illumination angle is known in the art as a retro-reflector. Retro-reflectors are common elements in street signs and highway lane markers where they serve to reflect the light from a car's headlights back to the driver. In U.S. Pat. No. 6,036,322, Nilsen describes the design and fabrication of retro-reflecting microstructures that can be produced in plastic sheets using conventional high-volume replication methods. One aspect of the present invention involves the use of a reflector, preferably a retro-reflector, with an SSR chemical sensor, to provide a sensitive chemical detection system that can be interrogated from a remote location. High-speed detection is achieved directly without the use of intermediate chemical labels such as fluorescent materials. The invention will find particular use in environmental applications such as the monitoring of the levels of algae-related toxins in lake water, and in military applications such as the remote detection of chemical warfare agents and explosives.

Another aspect of the present invention is directed towards such an SSR chemical sensor that provides a sensitive chemical sensor that can be interrogated from a remote location using an interrogating light beam that strikes the SSR sensor at non-normal incidence.

Another aspect of the present invention is directed towards an array of such SSR chemical sensors that provides a sensitive chemical sensor for a multitude of chemicals.

These aspects are generally achieved by providing a guided-mode SSR filter that is formed of dielectric bodies of various predetermined shapes such as lines, or elliptical or rectangular posts or holes repeated over the surface of a substrate and arranged in a predetermined pattern such as with an asymmetric grating or a symmetric two dimensional array such as a square grid or honeycomb, hexagonal grid. It is noted that the term "body" as used herein may include "holes" filled with air or some other dielectric material. The SSR device is then coated with a chemical capture material, or an array of different chemical capture materials specific to the chemical to be detected, using a variety of conventional chemical application methods. The complete SSR sensor is then located in front of a large-scale reflector, preferably a retro-reflecting device such as a corner cube, or in a preferred embodiment, laminated on top of an array of retro-reflecting microstructures.

In one application, an SSR sensor is integrated with a corner cube retro-reflector and placed in an enclosed high humidity environment. A light beam is directed from a source outside the enclosed environment into the environment containing the retro-reflecting SSR. A measure of the concentration of water molecules in the air within the enclosed environment can be obtained as a shift in the wavelength that resonates with the SSR in response to water condensing on the surface of the SSR. The observation is enabled using the light that transmits through the SSR and is returned to the source point through retro-reflection from the corner cube.

In another application, an SSR sensor is fabricated in plastic and laminated with a retro-reflecting micro-prism array that is also fabricated in one surface of a plastic sheet. The surface structures of the SSR sensor are then coated with a thin layer of material that is designed to chemically bind or adhere to one specific target chemical. Such a material is known as a receptor layer, or capture agent, and can be a MIP layer designed to maintain its receptor function in an aquatic environment. The MIP layer is designed to capture only microcystin, an aquatic cyanobacterial toxin generated by blue-green algae that is hazardous to humans. The retro-reflecting SSR with MIP layer is then placed on the shore of a lake or stream providing a means for monitoring the levels of microcystin in the lake water from a remote location.

In another application, a retro-reflecting SSR system coated with a capture agent specific to TNT can be deployed ahead of a military unit to detect the presence of explosives such as land mines.

These advantages of the present invention will become more apparent from the following specification and claims.

This invention features an apparatus for remotely detecting the presence and concentration of matter in contact with a surface structure optical filter by observation of a shift in the wavelength of filtered electromagnetic waves, the apparatus comprising a first substrate having a surface relief structure containing at least one dielectric body with at least one physical dimension smaller than the wavelength of the filtered electromagnetic waves, such structures repeated in a one or two dimensional array covering at least a portion of the surface of the first substrate. The surface relief structure are composed of or covered by a material sufficient to form a guided mode resonance filter. There is also a retro-reflecting structure that reflects and redirects the electromagnetic waves transmitted through the first substrate back through the first substrate in a direction substantially parallel to the propagation direction of the filtered electromagnetic waves. When a sample material is deposited on the surface relief structures, an observable shift in the wavelength of the filtered electromagnetic waves is produced that is in proportion to the amount of sample material accumulated.

Also featured in the invention is an apparatus for remotely detecting the concentration of matter in a material layer by observation of a shift in the wavelength of filtered electromagnetic waves, the apparatus comprising a substrate having a surface relief structure containing at least one dielectric body with at least one physical dimension smaller than the wavelength of the filtered electromagnetic waves, such structures repeated in a one or two dimensional array covering at least a portion of the surface of the substrate, a material coating the surface relief structures of the substrate to form a guided mode resonance filter, a material layer over the material coating and which adheres, chemically binds, or chemically reacts to a sample material thereby producing an observable shift in the wavelength of the filtered electromagnetic waves, and a retro-reflecting structure that reflects and redirects the electromagnetic waves transmitted through the first substrate back through the first substrate in a direction substantially parallel to the propagation direction of the filtered electromagnetic waves. The top material layer may be a selective capture layer comprised of biomolecules such as protein, nucleic acids, lipids, saccharides, and other biomolecular species, which have selective affinity for target molecules. The top material layer may be a selective capture layer comprised of organic or inorganic molecules with selective affinity for target molecules. The top material layer may be a selective capture layer comprised of molecularly imprinted polymers (MIPs) with selective affinity for target molecules.

The spacing of the surface relief structures in the arrays may be substantially the same, and less than the wavelength of the filtered electromagnetic waves. The dimensions of and the composition of the surface relief structures in the arrays may produce more than one range of wavelengths of filtered electromagnetic waves. The individual dielectric bodies in the surface relief structures may be arranged in a two dimensional array forming a honeycomb pattern with circular symmetry. The individual dielectric bodies in the surface relief structures may be arranged in a one-dimensional array forming a grating pattern. The individual dielectric bodies in the surface relief structures may be circularly shaped.

The substrate may be made of glass, plastic, or epoxy, for example. The propagation direction of electromagnetic waves resonantly reflected from the surface structures, or transmitted through the substrate, is preferably not altered by the accumulation of sample material on the surface structures. The retro-reflecting structure may be configured as a single corner-cube with dimensions much larger than the area illuminated by the electromagnetic waves. Alternatively, the retro-reflecting structure may be configured as a one- or two-dimensional array of micro prisms.

The individual dielectric bodies comprising the surface texture may have conical, elliptical, square, rectangular, sinusoidal, hexagonal, or octagonal cross sectional profiles. Alternatively, the individual dielectric bodies comprising the surface texture may be lines with a width less than the wavelength of the filtered electromagnetic waves and a length substantially equivalent to the substrate dimension, repeated in an array with a spacing less than the wavelength of the filtered electromagnetic waves. The dielectric bodies comprising the surface relief structures may be comprised of a material selected from the group consisting of zinc sulfide, titanium oxide, tantalum oxide, and silicon nitride. The surface relief structures may comprise a conductive material. The apparatus may further comprise means for applying a voltage to the surface relief structure to produce an electric field. The apparatus may further comprise a second resonant structure proximate the first substrate to provide a static reference signal which can be used to determine the difference between a shifted signal due to a deposited material layer and a shifted signal due to varying ambient conditions.

The sample material may comprise an organic substance or an inorganic substance, or a biochemically-derived substance.

BRIEF DESCRIPTION OF THE DRAWINGS

FIG. 1 is a cross sectional diagram of a retro-reflecting chemical sensor according to certain principles of the present invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
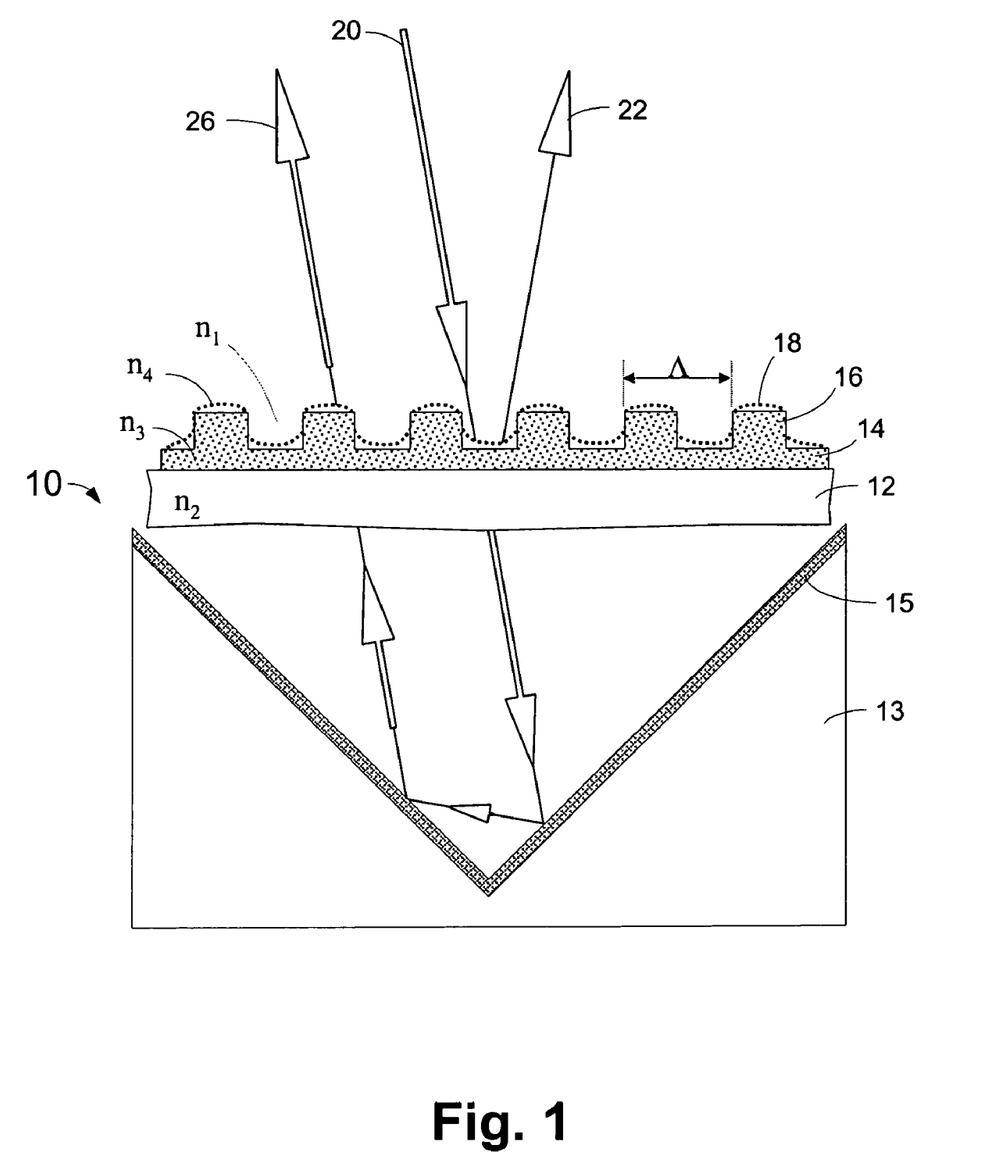

Device 10, shown in the cross sectional diagram of FIG. 1, operates on illuminating light 20 that contains a spectral content that includes a range of wavelengths that resonate with the surface structures 16. Illuminating light 20 is transmitted through the surface texture 16 containing uniform layer 14 supported by substrate 12 where it reflects off the surface 15 of the corner cube retro-reflector 13. The retro-reflector surfaces serve to redirect transmitted light 20 upon reflection so as to propagate back through substrate 12 and surface texture 16 in a direction that is opposite to and parallel with illuminating light 20, emerging as retro-reflected light 26. Retro-reflected light 26 contains the same spectral content as illuminating light minus the range of wavelengths that resonate with the surface structure waveguide and are reflected as light beam 22.

The chemical sensing surface structure optical filter is built upon a platform or substrate 12 with an optical index of refraction n2. The filter consists of a uniform material layer 14 with refractive index n3 and a surface relief structure 16 configured as a close-packed two-dimensional array of columns or posts with a rectangular cross sectional profile also made of a material with refractive index n3. The posts could have other cross-sectional shapes set forth above, such as circular. The surface relief structure can be composed of a conductive material. This allows the application of an electric field through the provision of a voltage source suitably connected to the device. The space between the posts 16 is filled with a material with refractive index n1. The posts 16 are repeated in an array across the surface of the uniform material layer 14 on substrate 12 with a periodic spacing, or pitch of Λ. The array of posts 16 may be arranged in a honeycomb pattern with circular symmetry, for example. To serve as a chemical sensing optical filter, the periodic spacing must be less than the wavelength of the light to be filtered. Such a grating is referred to as 'sub-wavelength' in the art. When a material layer 18 with refractive index n4 begins to accumulate on the surface structures 16, the wavelength of light that resonates with the structures 16 is shifted in an amount that is proportional to the amount of material that has deposited on the structures, and is reflected as light beam 22. In addition, the surface structure filter must be fabricated with materials that form a waveguide. This requires that the refractive index of the material layers are such that n2<n3>n1, and n3≧n4.

Figure 2:
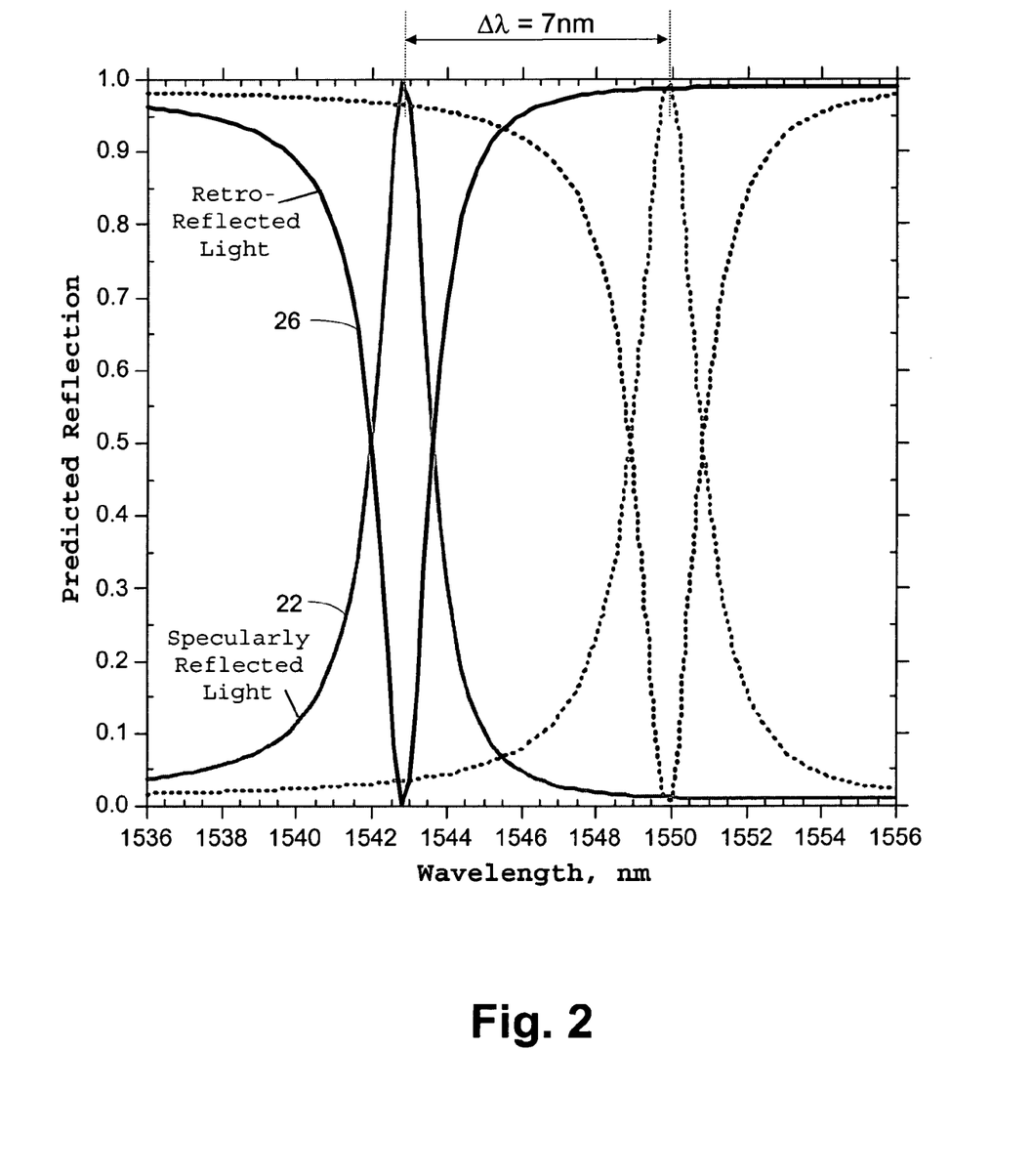
FIG. 2 is a plot showing the theoretical performance of the retro-reflecting chemical sensor of FIG. 1 when illuminated by light incident at 10 degrees.

The performance of the chemical sensing surface structure optical filter design 10 is simulated using a rigorous vector diffraction calculation. The software simulation predicts the spectral reflectance and transmittance of broad spectrum light through a user defined three-dimensional surface texture composed of multiple structured and uniform materials. The calculation accounts for arbitrary polarization states and light incident angles. Measured data for the optical constants of a library of materials is included. FIG. 2 shows a plot of the predicted performance of the chemical sensing filter design shown in FIG. 1. The model employed tantalum pentoxide (Ta2O5) with n3=2.1 for of chemical sensor device 10 can be determined from a remote location and over a wide range of observation angles.

Figure 4:
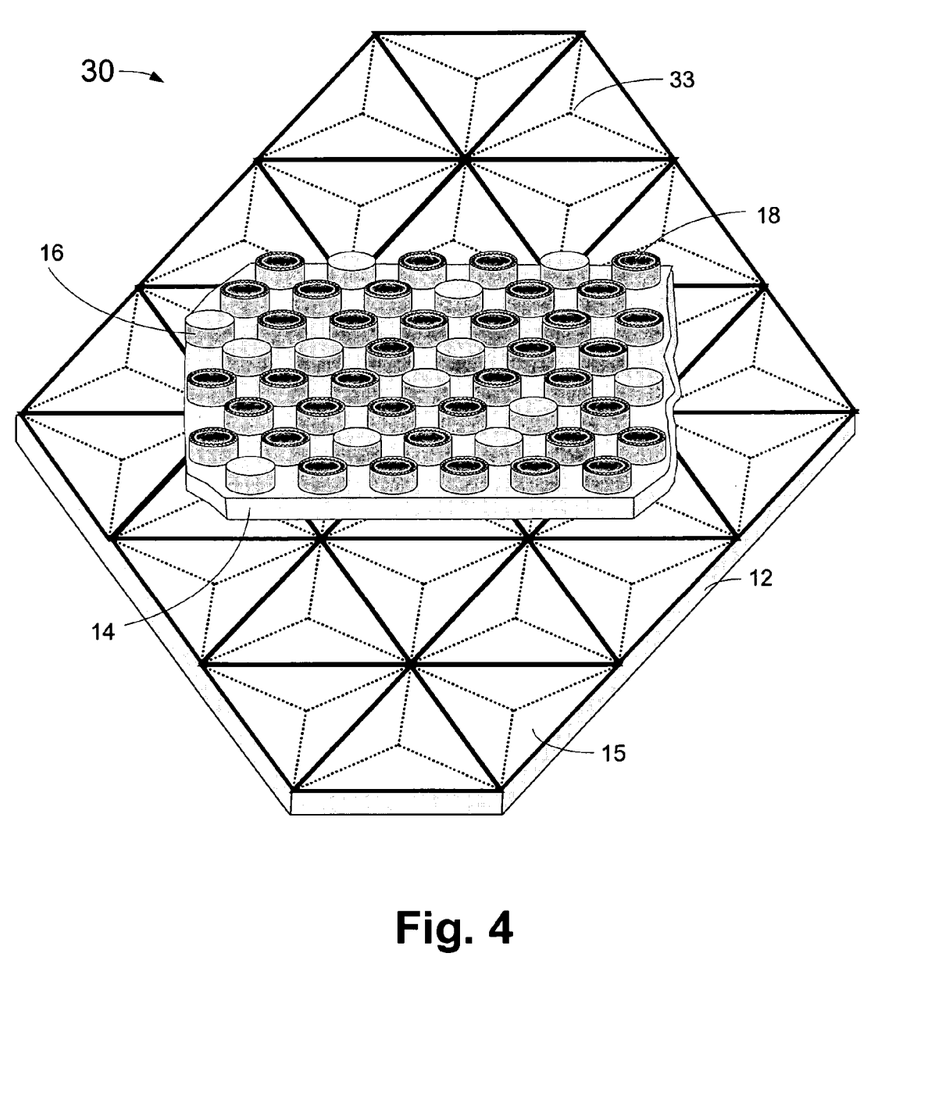
FIG. 4 is a diagram showing an elevation view of a retro-reflecting chemical sensor according to certain principles of the present invention.
Figure 5:
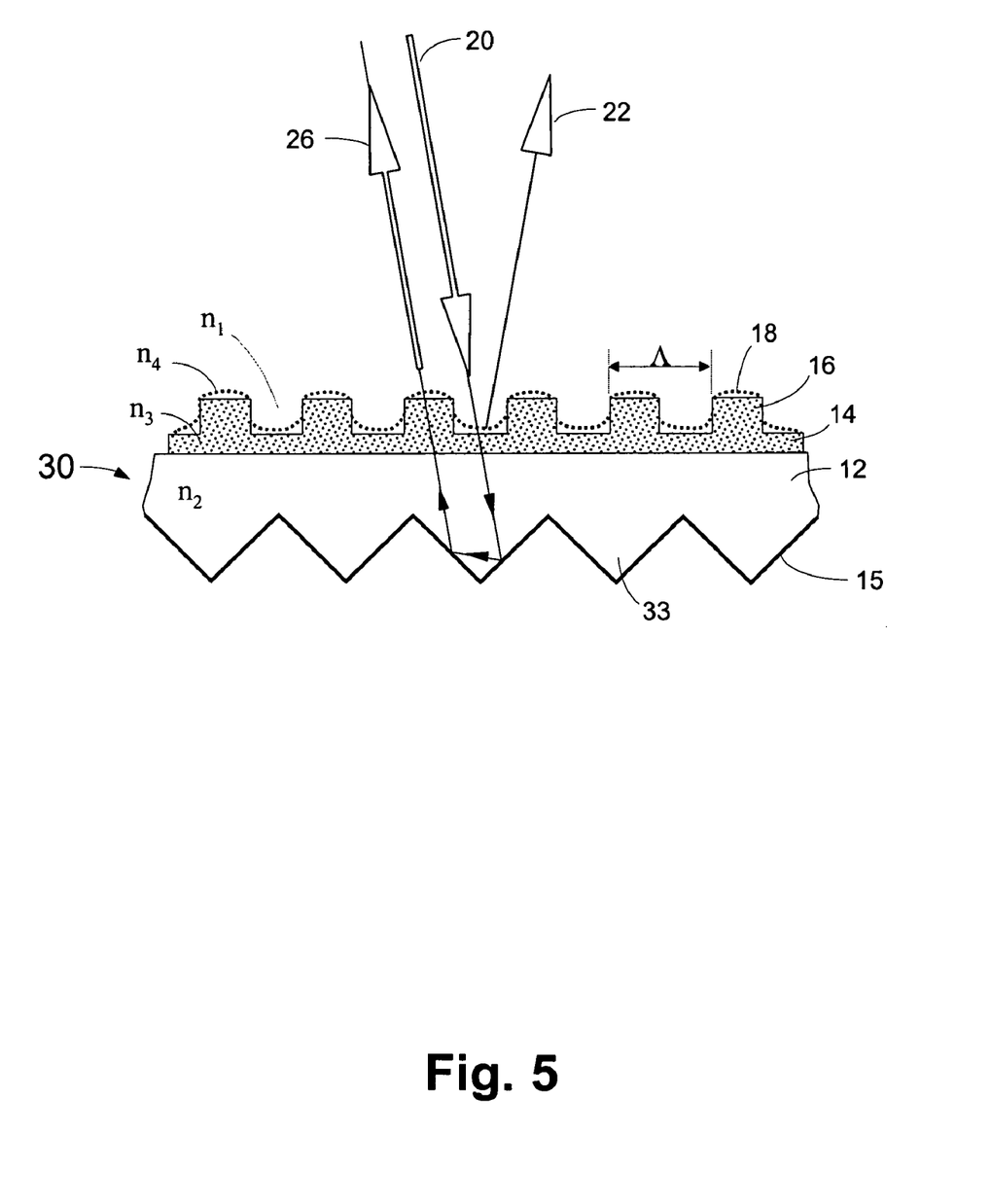
FIG. 5 is a cross sectional diagram of the retro-reflecting chemical sensor of FIG. 4.

One large retro-reflecting corner cube is not practical in many applications. An array of retro-reflecting microstructures fabricated in a thin substrate can provide the same function as a single large corner cube. Such a corner cube array can be fabricated in one surface of a substrate such as plastic, with the SSR sensor structures fabricated in the opposite surface. FIGS. 4 and 5 show elevation and cross sectional views of chemical sensing device 30 incorporating an array of microstructure prisms. FIGS. 4 and 5 show the same honeycomb arrangement of posts 16 fabricated on a uniform material layer 14 as the FIG. 1 device 10, but retro-reflecting component 13 of device 10 is replaced by a close packed triangular array of retro-reflecting microstructure prisms 33. The faces of the microstructure prisms are coated with material layer 15 that is used to modify the light reflectance to satisfy a particular application. In a typical application material layer 15 is a highly reflecting material such as a metal or a dielectric film stack. The microstructure prisms 33 and the resonant structures 16 and 14, are built upon opposite surfaces of substrate 12. FIG. 5 shows that the array of microstructure prisms 33 serve to produce retro-reflected light 26 in a manner that is functionally equivalent to the large scale corner cube 13 of device 10.

Figure 6:
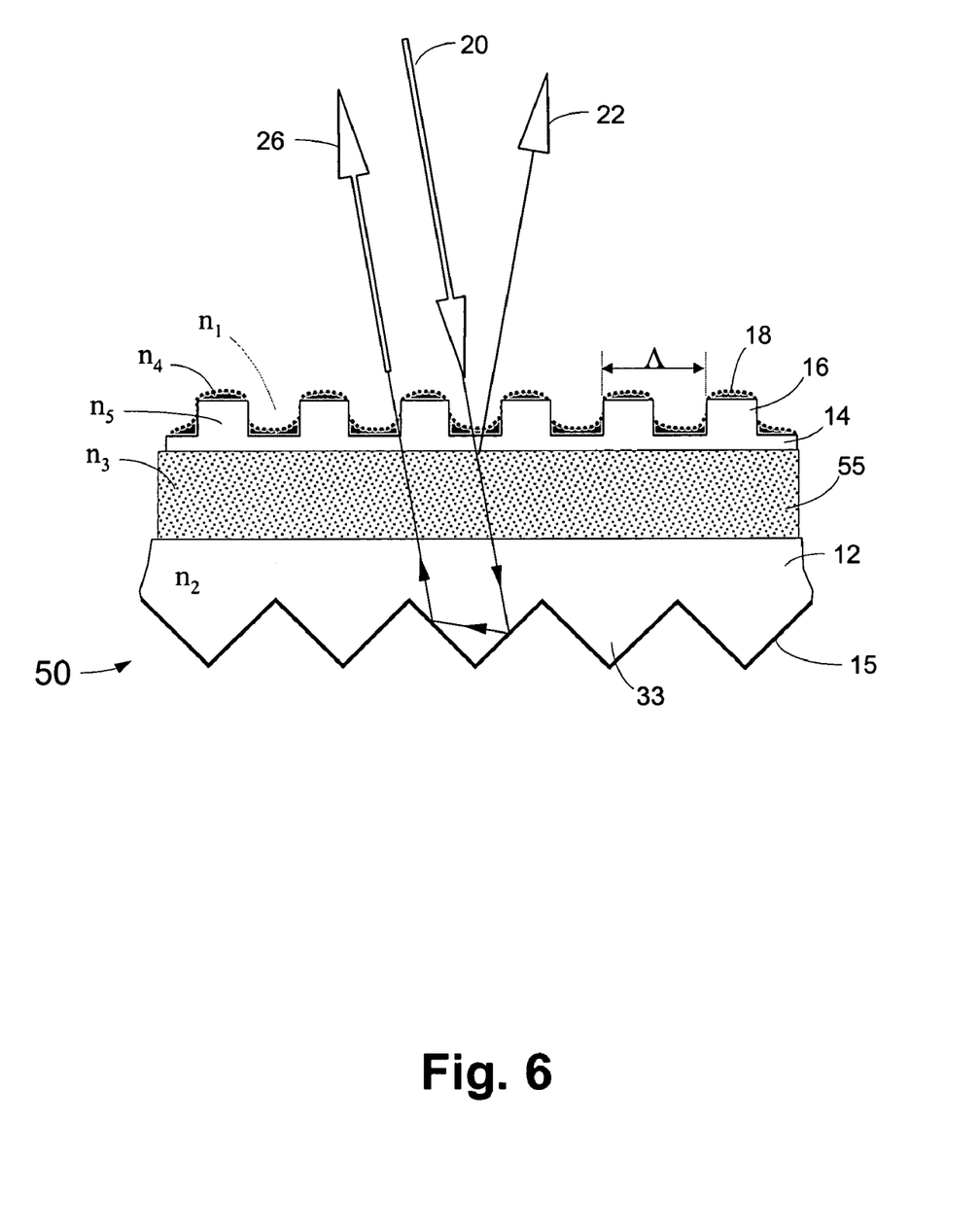
FIG. 6 is a cross sectional diagram showing another embodiment of a retro-reflecting chemical sensor according to certain principles of the present invention.

FIG. 6 shows device 50, an alternative embodiment for the chemical sensor structure incorporating microstructure prisms 33. In this design, a thick uniform material layer 55 with refractive index n3 is inserted between surface structures 16 containing uniform layer 14 and substrate 12. Layer 55 serves as the needed waveguide when the refractive index of the surrounding layers satisfies the condition n2<n3>n1, and n3≧n4 or n5. The resonant condition in layer 55 is satisfied by two wavelength ranges, and material layer 14 and surface structures 16, an accumulating material with n4=1.48, a glass substrate with n2=1.48, and an environment of air with n1=1. The honeycomb grating pitch, A, was set to 880 nm, and the width and height of the posts was set at 350 nm and 175 nm respectively. The thickness of the Ta2O5 layer 14 was set at 340 nm. With the angle of the illuminating light set at 10 degrees, the model predicts that light with a wavelength of 1543 nm will be reflected from the filter structures as light beam 22 indicated by the solid grey line on the plot, propagating at an angle of 10 degrees on the opposite side of the normal to illuminating light 20. All other wavelengths will be transmitted through the filter and undergo retro-reflection by device 13 emerging as light beam 26 as indicated by the solid black line in the figure. In this case the simulation was conducted before material layer 18 begins to accumulate—the initial sensor response. The dashed lines in the plot show the effect on specularly reflected light 22 and retro-reflected light 26 after a 20 nm thick layer of material 18 has been deposited. The resonant wavelength shifts to 1550 nm in response to the addition of material layer 18. In this way device 10 serves as a chemical detector that can be interrogated by light beam 20 and read by observing the spectral notch position of the return light 26.

Figure 3:
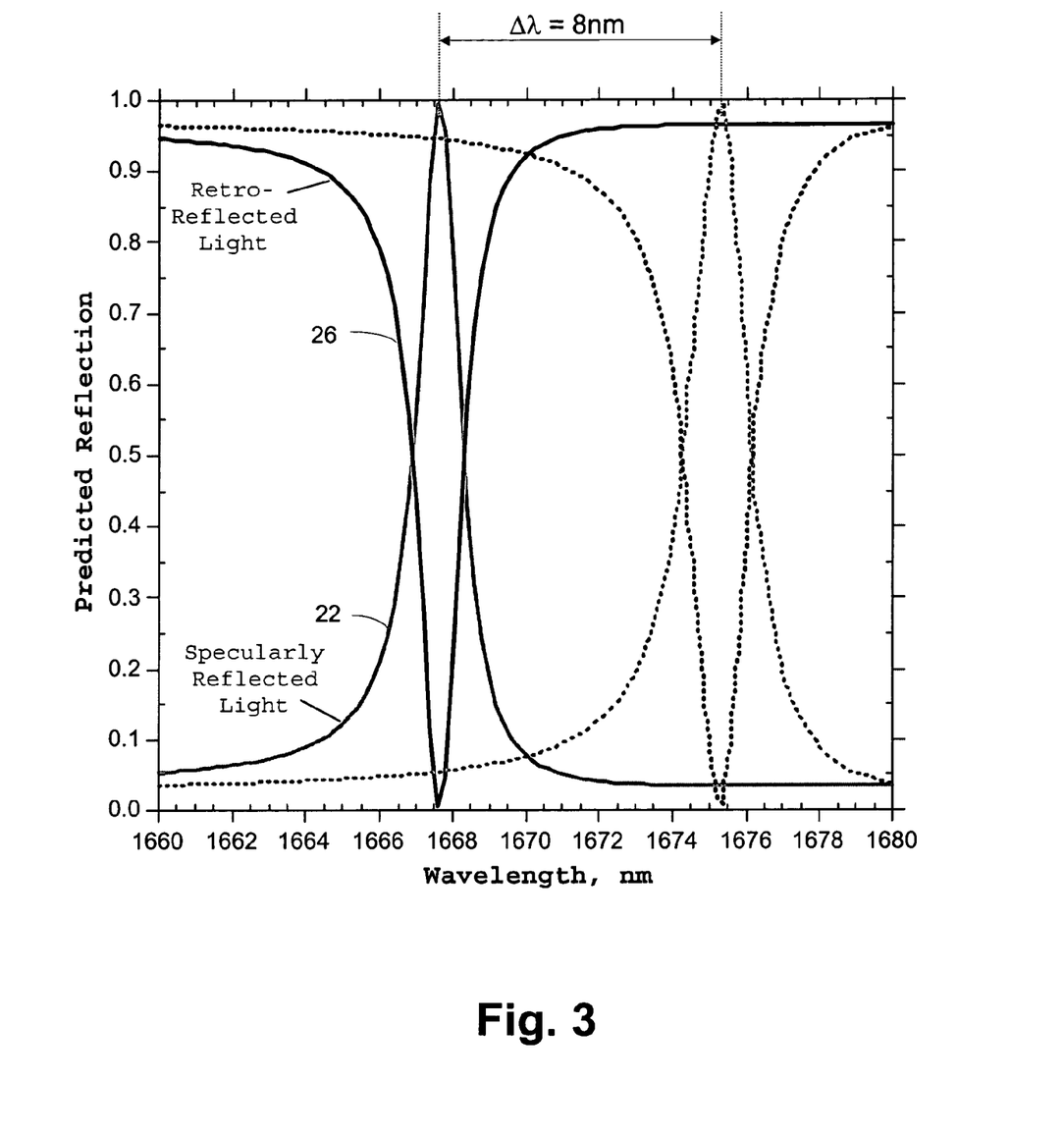
FIG. 3 is a plot showing the theoretical performance of the retro-reflecting chemical sensor of FIG. 1 when illuminated by light incident at 20 degrees.

FIG. 3 shows the theoretical response of chemical sensor device 10 when illuminating beam 20 is incident at 20 degrees. The resonance condition is now satisfied by a longer wavelength and reflected light 22 contains a narrow range of wavelengths centered at 1667.5 nm. Retro-reflected light 26 again returns back to the source point of illuminating light 20 with no energy at the 1667.5 nm wavelength. As in FIG. 2, the response to a 20 nm accumulation of material 18 can be observed as a shift in the spectral notch in retro-reflected light 26. By transmitting a broad range of wavelengths in the near infrared, the response device 50 will generate a reflected beam 22 that contains two spectral components. Retro-reflected light 26 will be returned without two spectral components. Device 50 then provides two channels of redundant information that can be useful in applications where one information channel is blocked or obscured.

Figure 7:
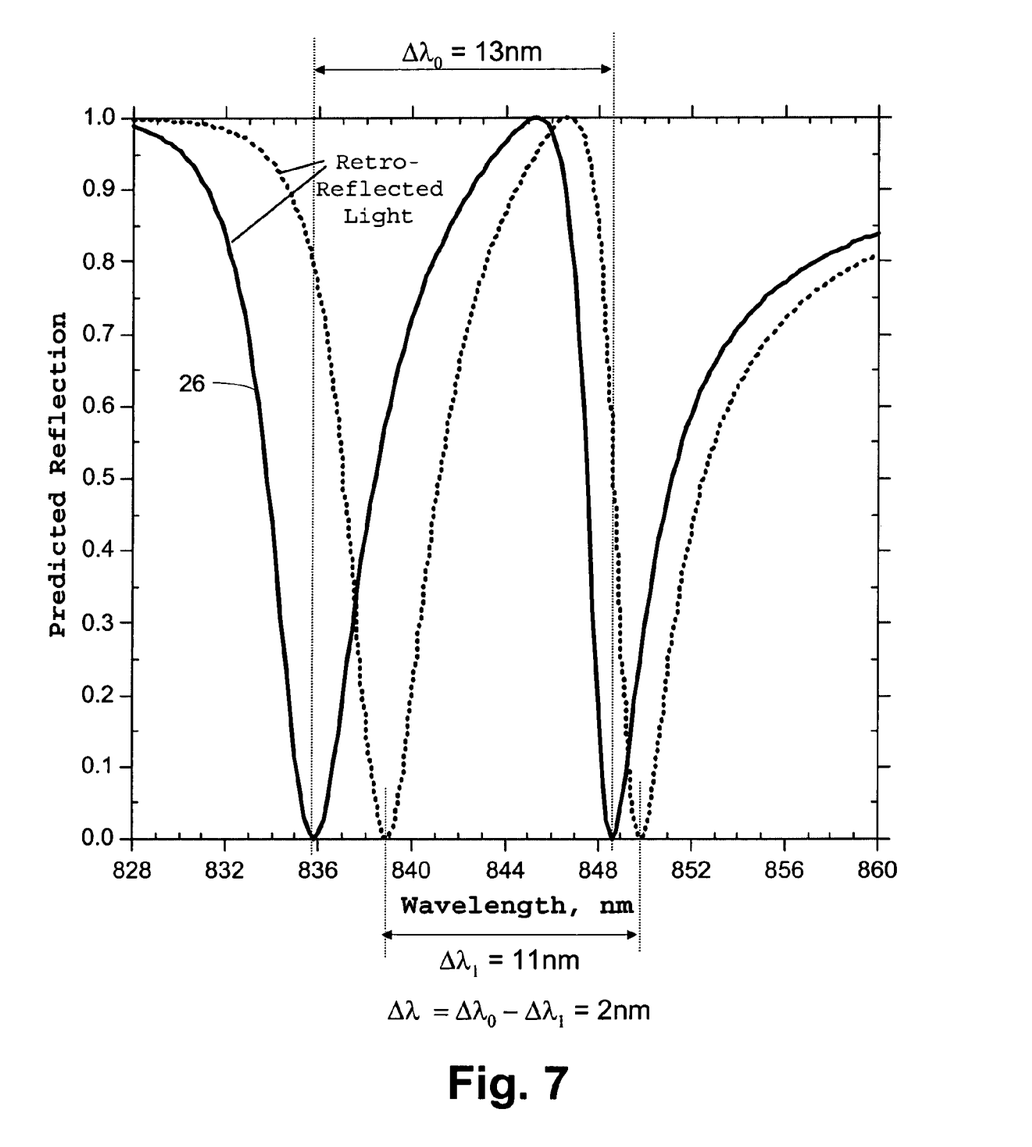
FIG. 7 is a plot showing the theoretical performance of the retro-reflecting chemical sensor of FIG. 6 when illuminated at an angle of incidence of 10 degrees.

FIG. 7 shows a plot of the predicted performance of the chemical sensing device 50 shown in FIG. 6. The model employed tantalum pentoxide (Ta2O5) for material layer 14 and surface structures 16 and waveguide layer 55 so that n3=n5=2.1, an accumulating material 18 with n4=1.48, a glass substrate 12 with n2=1.48, and an environment of air with n1=1. A honeycomb array of post structures is again modeled with a pattern pitch, A, set to 480 nm, and the width and height of the posts set at 145 nm and 120 nm respectively. The thickness of the Ta2O5 waveguide layer 55 was set at 400 nm and the uniform layer 14 was set to a thickness of zero. With the angle of the illuminating light 20 set at 10 degrees, the model predicts that light with wavelengths of 836 nm and 849 nm will be reflected from the filter structures as light beam 22. All other wavelengths will be transmitted through the filter structures and undergo retro-reflection by the microstructure prism array 33 emerging as light beam 26 as indicated by the solid black line in the figure. As in FIGS. 2 and 3, the simulation was conducted before material layer 18 begins to accumulate, showing the static sensor response. The dashed line in the plot shows the effect on retro-reflected light 26 after a 20 nm thick layer of material 18 has been deposited. The resonant wavelengths shift to 839 nm and 850 nm in response to the addition of material layer 18. As shown in the figure, the two notch positions can be read independently to determine a chemical concentration, or a differential measurement can be made using both notches at one time.

Figure 8:
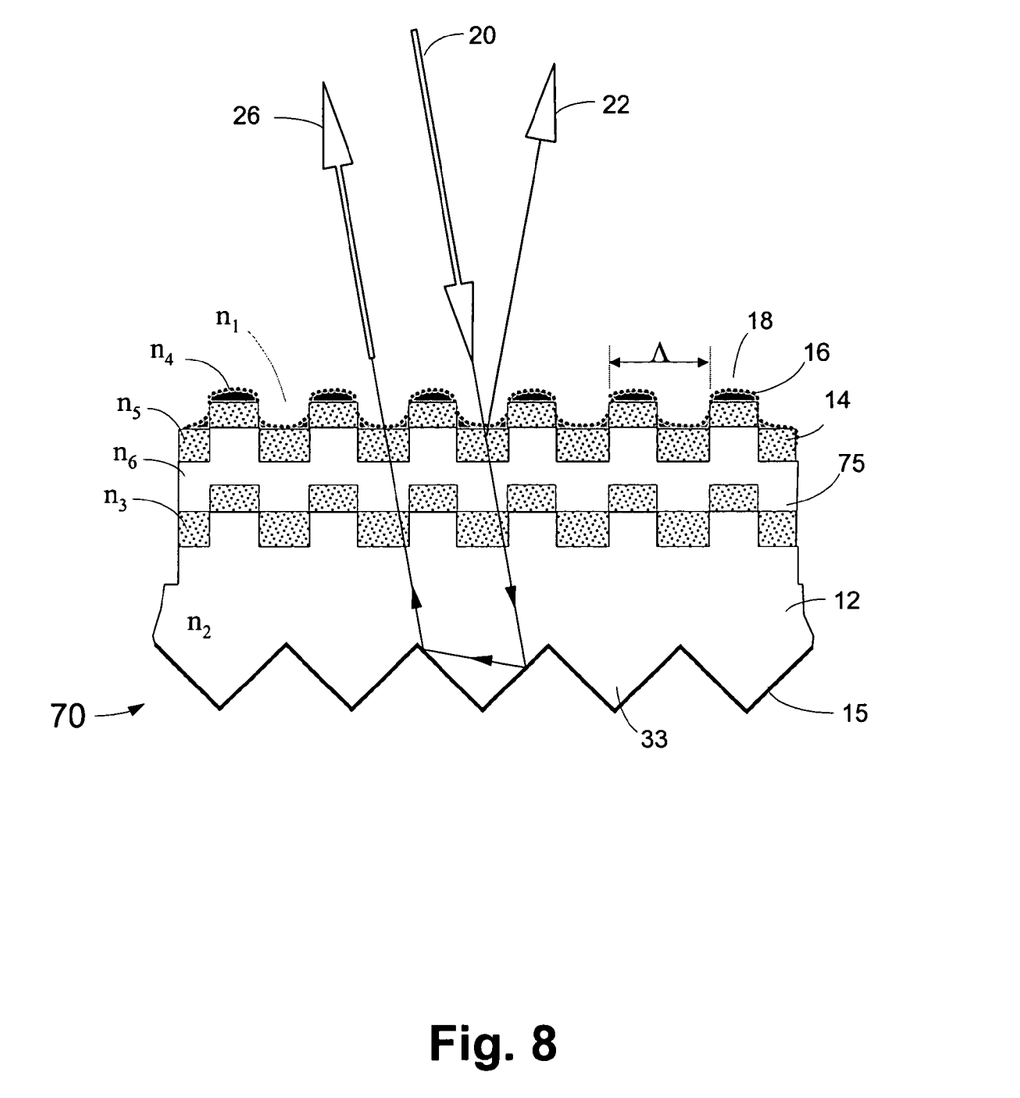
FIG. 8 is a cross sectional diagram showing another embodiment of a retro-reflecting chemical sensor according to certain principles of the present invention.

As described in U.S. Pat. Nos. 6,791,757 and 6,870,624, a secondary resonant structure can be embedded below the surface structure upon which a chemical deposits to provide a static reference wavelength that is not disturbed by the accumulation of the target chemical. By observing an increase in the separation of the two spectral components reflected by the doubly resonant structure, environmental factors such as temperature that effect the resonant wavelength, can be eliminated. Such a self referencing sensor design combined with a retro-reflecting microstructure prism array, is shown as device 70 in FIG. 8, and has secondary resonant structure 75 embedded below the surface structure.

Figure 9:
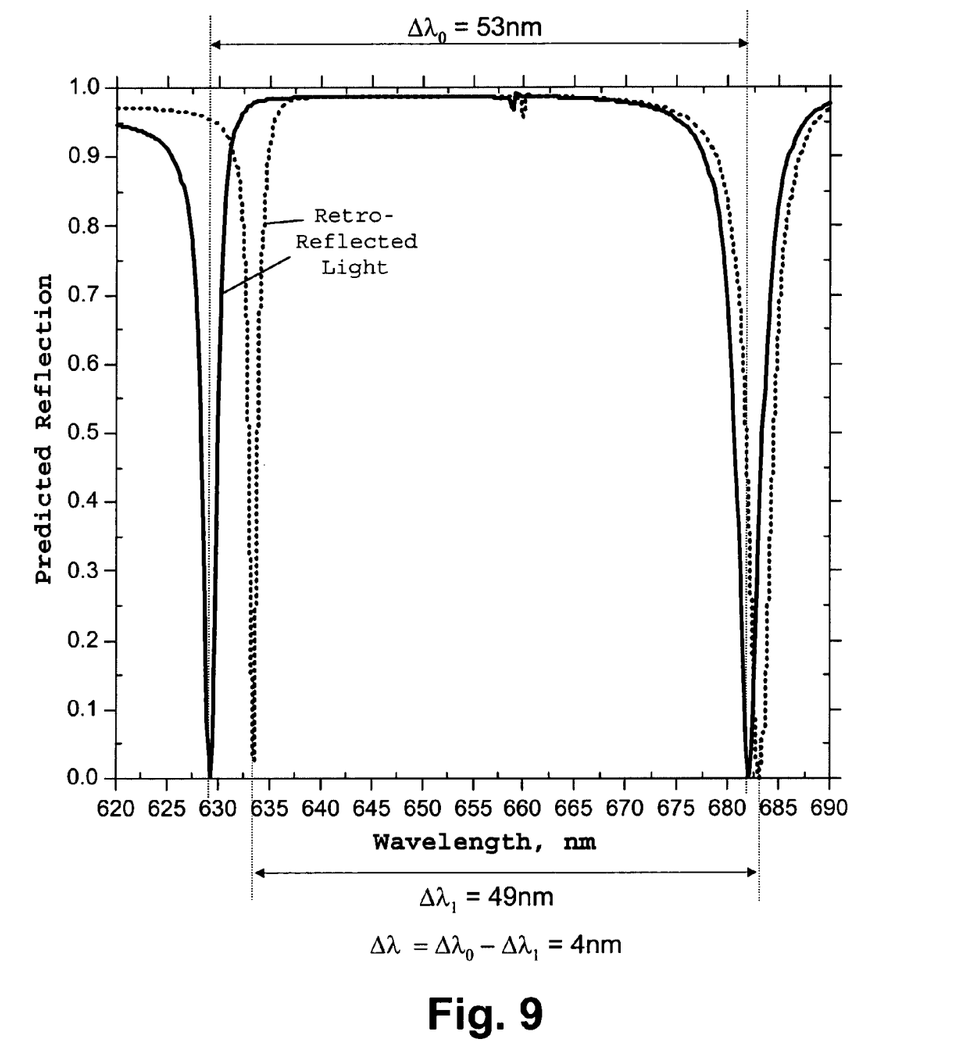
FIG. 9 is a plot showing the theoretical performance of the retro-reflecting chemical sensor of FIG. 8 when illuminated at an angle of incidence of 10 degrees.

FIG. 9 shows a plot of the theoretical performance of device 70 where as with previous examples illuminating light 20 is incident at 10 degrees. Again the solid black curve represents the response of device 70 before accumulation of material layer 18, and the dashed grey line shows the response after 20 nm of material layer 18 has been deposited onto the top surface structures 16. The materials modeled were again Ta2O5 for structures 16, 14, and 75 so that n3=n5=2.1, glass for substrate 12 with n=1.48, a polymer separation layer between structures 75 and 16 with n6=1.48, and an accumulating material layer 18 with n4=1.48. The pitch of the array of posts comprising surface structure 16 and embedded structure 75 was set at 410 nm, with the width and height of the posts set at 200 nm and 130 nm respectively. The separation between structural layers was set at 100 nm. The calculation shows that device 70 will resonate at wavelengths of 629 nm and 681.5 nm with no accumulation. When material layer 18 reaches a thickness of 20 nm, the resonance associated with the embedded structure shifts only slightly to 682.5 nm, while the resonant wavelength for the top structures in contact with material layer 18 has shifted to 633 nm. A change in the temperature of device 70 can also shift the resonant wavelength, but the shift would be equal for both resonant wavelengths. A difference measurement then isolates a wavelength shift due to chemical accumulation from environmental factors.

Figure 10:
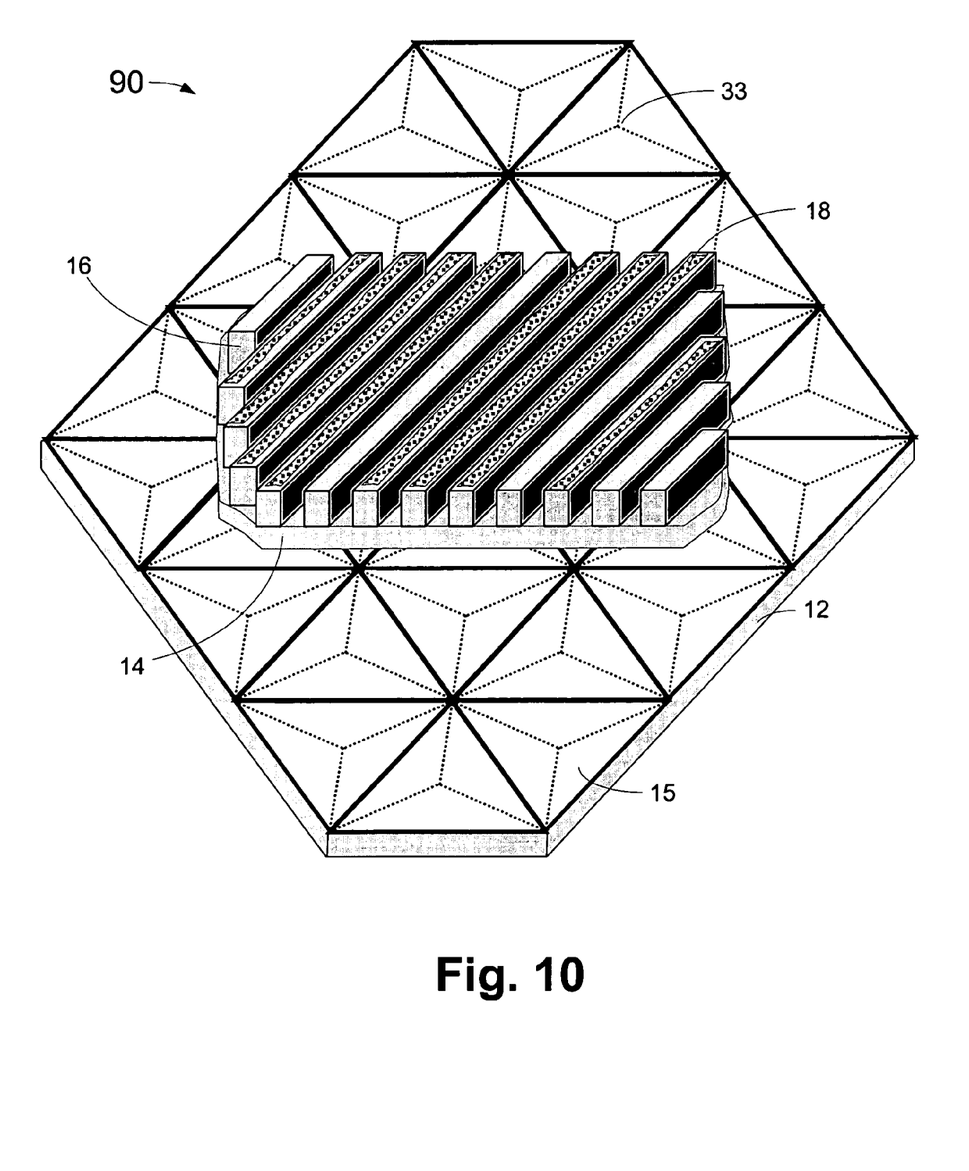
FIG. 10 is a diagram showing an elevation view of a polarization selective retro-reflecting chemical sensor according to certain principles of the present invention.

Asymmetric resonant structures can also be used to further isolate the chemical sensing signal onto channels that are defined by the polarization state of the illuminating light. FIG. 10 shows device 90 incorporating an asymmetric surface structure chemical sensor in combination with a retro-reflecting microstructure prism array. The surface structures 16 in device 90 are rectangular profile lines repeated in a one-dimensional array with a pitch of 490 nm. Illuminating light 20 will resonate at one wavelength for light polarized substantially parallel to the long dimension of the grating lines, and at a different wavelength for light polarized substantially perpendicular to the grating lines. Note that the use of the identifiers 'S' and 'P' refer to orthogonal electric field orientations in all that follows, with S meaning an electric field vibrating parallel to the long dimension of the surface structures, and P designating an electric field vibrating in the orthogonal direction, or perpendicular to the long dimension of the surface structures.

Figure 11:
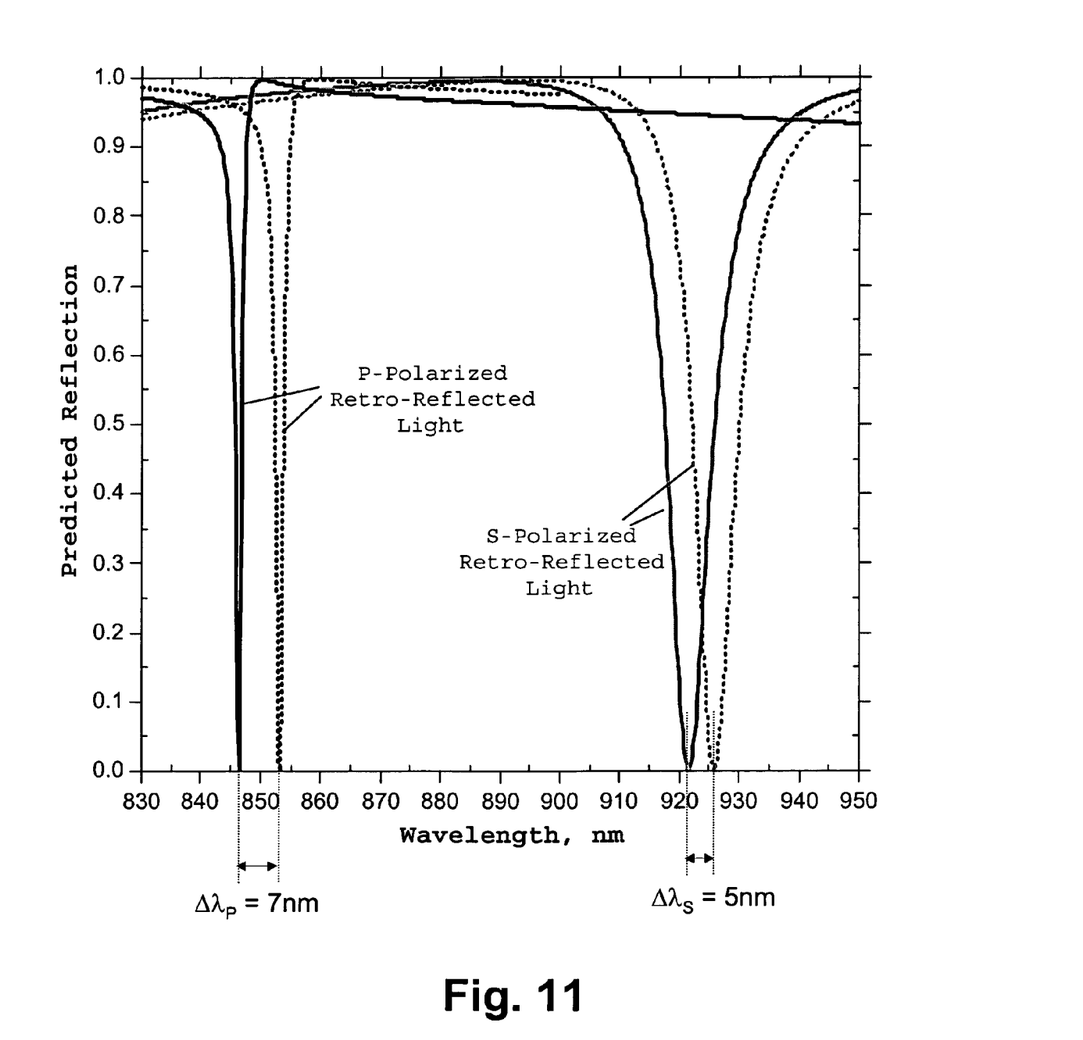
FIG. 11 is a plot showing the theoretical performance of the polarization selective retro-reflecting chemical sensor of FIG. 10 when illuminated at an angle of incidence of 10 degrees.

For a cross section taken in the P-polarization direction, device 90 appears identical to the cross section of device 30 of FIG. 5. FIG. 11 shows a plot of the predicted performance of the chemical sensing device 90 shown in FIGS. 5 and 10. The model employed Ta2O5 for material layer 14 and surface structures 16 with n3=2.1, an accumulating material 18 with n4=1.48, a glass substrate 12 with n2=1.48, and an environment of air with n1=1. The width and height of the grating lines was set at 200 nm and 125 nm respectively. The thickness of uniform layer 14 was set to 175 nm. With the angle of the illuminating light 20 set at 10 degrees, the model predicts that only P-polarized light at a wavelength of 846 nm (solid black line) and S-Polarized light at a wavelength of 921 nm (solid grey line) will be reflected from the filter structure as light beam 22. All other wavelengths will be transmitted through the filter structures and undergo retro-reflection by the microstructure prism array 33 emerging as light beam 26 which is shown in the plot. Again the simulation was conducted before material layer 18 begins to accumulate, showing the static sensor response. The dashed lines in the plot show the effect on retro-reflected light 26 after a 20 nm thick layer of material 18 has been deposited. The resonant wavelengths shift to 854 nm for P-polarized light (dashed black line), and to 926 nm for S-polarized light (dashed grey line) in response to the addition of material layer 18. Device 90 serves as a chemical sensor with two channels of information that are selected by the polarization state of illuminating light 20.

Although specific features of the invention are shown in some drawings and not others, this is for convenience only as the features may be combined in other manners in accordance with the invention. Other embodiments will occur to those skilled in the art and are within the following claims:

What is claimed is:

1. An apparatus for remotely detecting the presence and concentration of matter in contact with a surface structure optical filter by observation of a shift in the wavelength of filtered electromagnetic waves, the apparatus comprising:
    a first substrate having a surface relief structure containing at least one dielectric body with at least one physical dimension smaller than the wavelength of the filtered electromagnetic waves, such structures repeated in a one or two dimensional array covering at least a portion of the surface of the first substrate;
    said surface relief structure being composed of or covered by a material sufficient to form a guided mode resonance filter; and
    a retro-reflecting structure that reflects and redirects the electromagnetic waves transmitted through the first substrate back through the first substrate in a direction substantially parallel to the propagation direction of the filtered electromagnetic waves;
    whereby when a sample material is deposited on the surface relief structures, an observable shift in the wavelength of the filtered electromagnetic waves is produced that is in proportion to the amount of sample material accumulated.

2. An apparatus as in claim 1, wherein the spacing of the surface relief structures in the array is substantially the same, and is less than the wavelength of the filtered electromagnetic waves.

3. An apparatus as in claim 1, wherein the dimensions of and the composition of the surface relief structures in the array produces more than one range of wavelengths of filtered electromagnetic waves.

4. An apparatus as in claim 1, wherein the individual dielectric bodies in the surface relief structure are arranged in a two dimensional array forming a honeycomb pattern with circular symmetry.

5. An apparatus as in claim 1, wherein the individual dielectric bodies in the surface relief structure are arranged in a one dimensional array forming a grating pattern.

6. An apparatus as in claim 1, wherein the individual dielectric bodies in the surface relief structure are circularly shaped.

7. An apparatus as in claim 1, wherein the propagation direction of electromagnetic waves resonantly reflected from the surface structures, or transmitted through the substrate, is not altered by the accumulation of sample material on the surface structures.

8. An apparatus as in claim 1, wherein the retro-reflecting structure is configured as a single corner-cube with dimensions much larger than the area illuminated by the electromagnetic waves.

9. An apparatus as in claim 1, wherein the retro-reflecting structure is configured as a one- or two-dimensional array of corner cube micro prisms.

10. An apparatus as in claim 1, wherein the individual dielectric bodies comprising the surface texture have conical, elliptical, square, rectangular, sinusoidal, hexagonal, or octagonal cross sectional profiles.

11. An apparatus as in claim 1, wherein the individual dielectric bodies comprising the surface texture are lines with a width less than the wavelength of the filtered electromagnetic waves and a length substantially equivalent to the substrate dimension, repeated in an array with a spacing less than the wavelength of the filtered electromagnetic waves.

12. An apparatus as in claim 1, wherein the substrate comprises glass, plastic, or epoxy.

13. An apparatus as in claim 1, wherein the dielectric bodies comprising the surface relief structure are comprised of a material selected from the group consisting of zinc sulfide, titanium oxide, tantalum oxide, and silicon nitride.

14. An apparatus as in claim 1, wherein the surface relief structure is a conductive material.

15. An apparatus as in claim 1 further comprising means for applying a voltage to the surface relief structure to produce an electric field.

16. An apparatus as in claim 1, further comprising a second resonant structure proximate the first substrate to provide a static reference signal which can be used to determine the difference between a shifted signal due to a deposited material layer and a shifted signal due to varying ambient conditions.

17. An apparatus as in claim 1, wherein the sample material comprises an organic substance.

18. An apparatus as in claim 1, wherein the sample material comprises an inorganic substance.

19. An apparatus as in claim 1, wherein the sample material comprises a biochemically-derived substance.

20. An apparatus for remotely detecting the concentration of matter in a material layer by observation of a shift in the wavelength of filtered electromagnetic waves, the apparatus comprising:
    a substrate having a surface relief structure containing at least one dielectric body with at least one physical dimension smaller than the wavelength of the filtered electromagnetic waves, such structures repeated in a one or two dimensional array covering at least a portion of the surface of the substrate;
    a material coating the surface relief structures of the substrate to form a guided mode resonance filter;
    a material layer over the material coating and which adheres, chemically binds, or chemically reacts to a sample material thereby producing an observable shift in the wavelength of the filtered electromagnetic waves; and
    a retro-reflecting structure that reflects and redirects the electromagnetic waves transmitted through the first substrate back through the first substrate in a direction substantially parallel to the propagation direction of the filtered electromagnetic waves.

21. An apparatus as in claim 20, wherein the spacing of the surface relief structures in the array is substantially the same, and is less than the wavelength of the filtered electromagnetic waves.

22. An apparatus as in claim 20, wherein the bodies comprising the surface relief structure are arranged in a two-dimensional pattern.

23. An apparatus as in claim 20, wherein the surface relief structure is composed of a conductive material.

24. An apparatus as in claim 20, further comprising a second resonant structure proximate the first substrate to provide a static reference signal which can be used to determine the difference between a shifted signal due to a deposited material layer and a shifted signal due to varying ambient conditions.

25. An apparatus as in claim 20, wherein the individual dielectric bodies comprising the surface texture have conical, elliptical, square, rectangular, sinusoidal, hexagonal, or octagonal cross sectional profiles.

26. An apparatus as in claim 20, wherein the individual dielectric bodies in the surface texture are lines with a width less than the wavelength of the filtered electromagnetic waves and a length substantially equivalent to the substrate dimension, repeated in an array with a spacing less than the wavelength of the filtered electromagnetic waves.

27. An apparatus as in claim 20, wherein the substrate comprises glass, plastic, or epoxy.

28. An apparatus as in claim 20, wherein the dielectric bodies comprising the surface relief structure are comprised of a material selected from the group consisting of zinc sulfide, titanium oxide, tantalum oxide, and silicon nitride.

29. An apparatus as in claim 20, wherein the sample material comprises an organic substance.

30. An apparatus as in claim 20, wherein the sample material comprises an inorganic substance.

31. An apparatus as in claim 20, wherein the retro-reflecting device is configured as a single corner-cube with dimensions much larger than the area illuminated by the electromagnetic waves.

32. An apparatus as in claim 20, wherein the top material layer is a selective capture layer comprised of biomolecules such as protein, nucleic acids, lipids, saccharides, and other biomolecular species, which have selective affinity for target molecules.

33. An apparatus as in claim 20, wherein the top material layer is a selective capture layer comprised of organic or inorganic molecules with selective affinity for target molecules.

34. An apparatus as in claim 20, wherein the top material layer is a selective capture layer comprised of molecularly imprinted polymers (MIPs) with selective affinity for target molecules.

* * * * *